United States Patent [19]
Conley et al.

[11] Patent Number: 5,527,325
[45] Date of Patent: Jun. 18, 1996

[54] ATHERECTOMY CATHETER AND METHOD

[75] Inventors: Daniel J. Conley, Redwood City; Mark E. Deem, San Francisco; Kent D. Dell, Redwood City; Bernard H. Andreas, Fremont, all of Calif.

[73] Assignee: Device for Vascular Intervention, Inc., Santa Clara, Calif.

[21] Appl. No.: 348,289

[22] Filed: Dec. 1, 1994

Related U.S. Application Data

[63] Continuation of Ser. No. 89,957, Jul. 9, 1993, abandoned.

[51] Int. Cl.⁶ ........................................ A61B 17/22
[52] U.S. Cl. ................................. 606/159; 604/282
[58] Field of Search ......................... 606/159; 604/22, 604/282

[56] References Cited

U.S. PATENT DOCUMENTS

| | | | |
|---|---|---|---|
| Re. 33,569 | 4/1991 | Gifford, III et al. | 606/159 |
| 3,485,234 | 12/1969 | Stevens. | |
| 4,669,469 | 6/1987 | Gifford, III et al. | 128/305 |
| 4,764,324 | 8/1988 | Burnham | 264/103 |
| 4,781,186 | 11/1988 | Simpson et al. | 128/305 |
| 4,898,591 | 2/1990 | Jang et al. | 604/282 |
| 4,926,858 | 5/1990 | Gifford, III et al. | 606/159 |
| 4,950,257 | 8/1990 | Hibbs et al. | 604/265 |
| 4,979,951 | 12/1990 | Simpson | 606/159 |
| 5,047,040 | 9/1991 | Simpson et al. | 606/159 |
| 5,071,425 | 12/1991 | Gifford, III et al. | 606/159 |
| 5,084,010 | 1/1992 | Plaia et al. | 604/22 |
| 5,092,873 | 3/1992 | Simpson et al. | 606/159 |
| 5,217,440 | 6/1993 | Frassica | 604/282 |
| 5,226,909 | 7/1993 | Evans et al. | 606/159 |
| 5,290,230 | 3/1994 | Ainsworth et al. | 604/282 X |

*Primary Examiner*—Michael H. Thaler
*Attorney, Agent, or Firm*—Townsend and Townsend and Crew

[57] ABSTRACT

An improved atherectomy catheter and methods of making and using a catheter are disclosed. In one embodiment, the catheter comprises a housing shaft having a torsionally-reinforced outer layer concentrically disposed over a polymeric inner layer, with an inflation tube disposed concentrically over the housing shaft to define an annular inflation lumen. A housing is attached to the distal end of the housing shaft, and may contain an interventional device such as a cutting blade. Apparatus for urging the housing against a vessel wall, such as a balloon, is attached to the housing opposite the an interventional device and is in communication with the inflation lumen. A drive shaft may be rotatably disposed through a longitudinal lumen in the housing shaft, the drive shaft being coupled at its distal end to the interventional device. The method of the invention facilitates construction of a catheter shaft through the steps of forming a flexible tubular polymeric outer layer with a first melting point over a tubular polymeric inner layer with a second melting point, the first melting point being lower than the second melting point; heating the outer layer to at least the first melting point and less than the second melting point, and impregnating a wire braid into the outer layer up to the inner layer. In a preferred embodiment, the inner layer is a fluorocarbon polymer, and the outer layer is a thermoplastic elastomer which is stable near body temperatures, impregnated with one or more layers of a stainless steel wire braid.

22 Claims, 10 Drawing Sheets

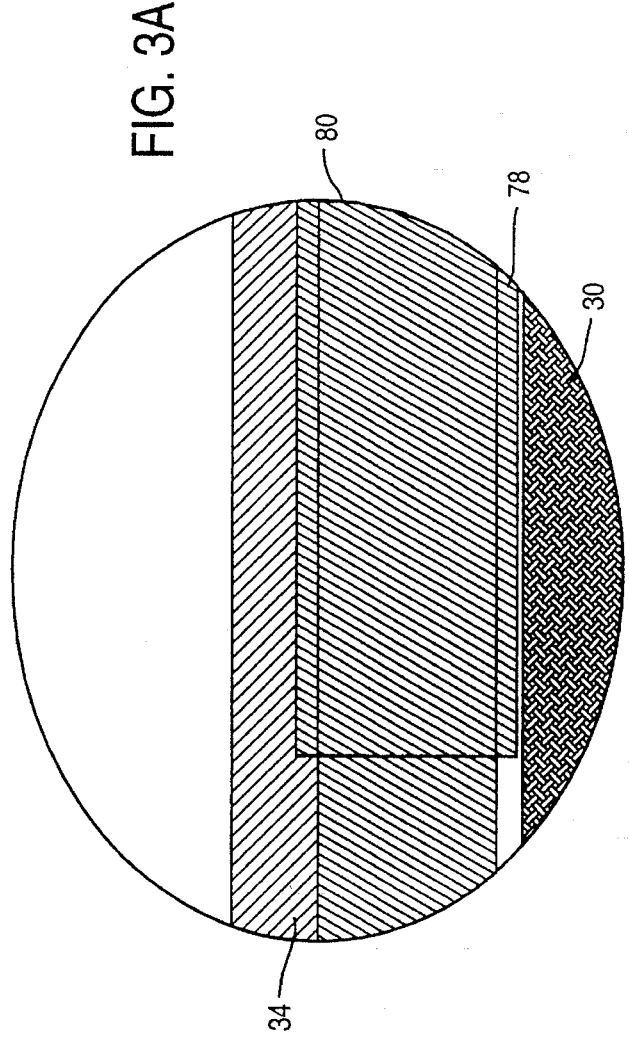
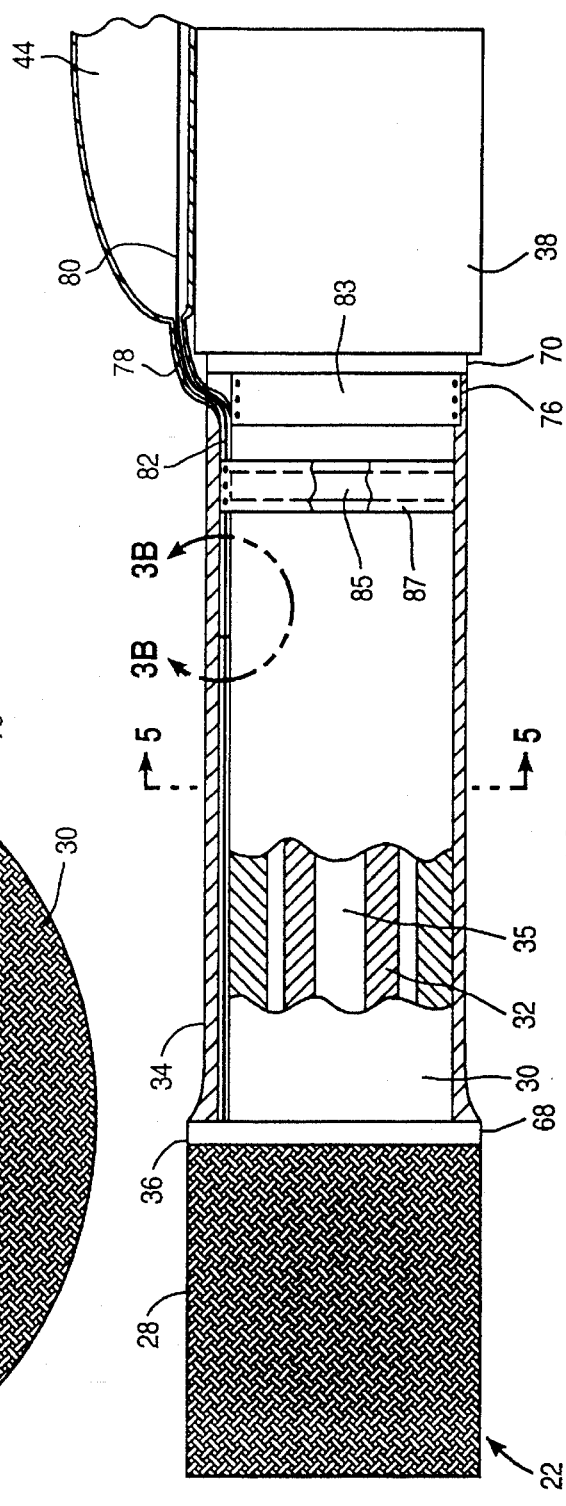

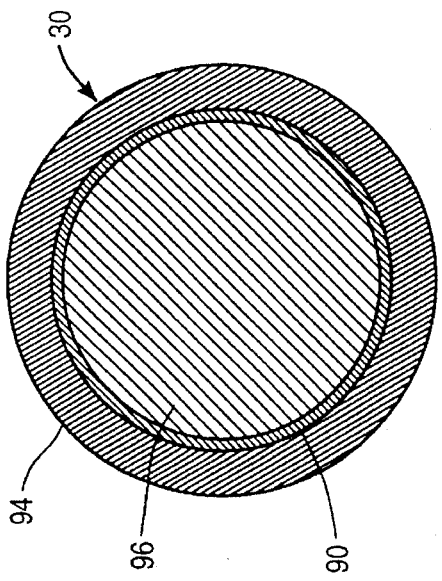
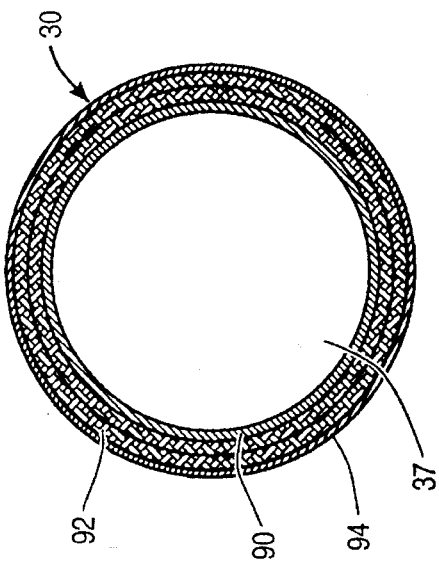
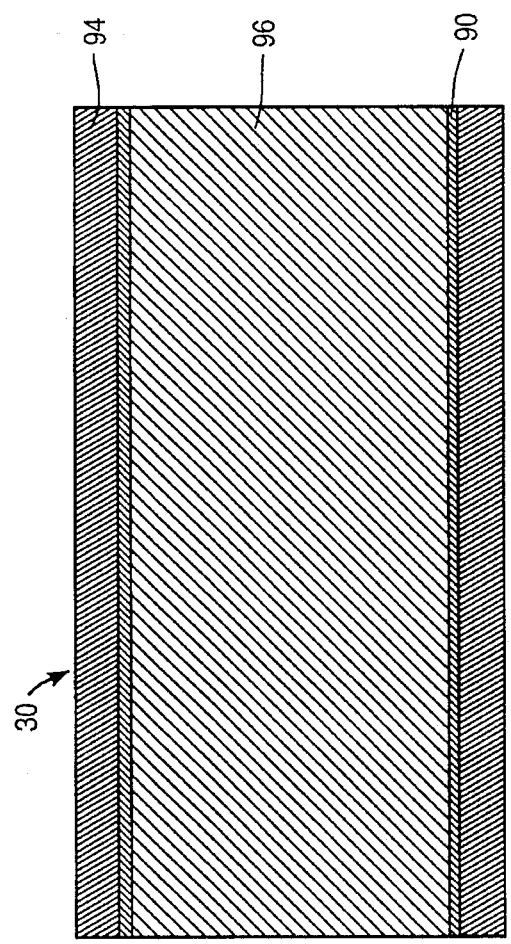
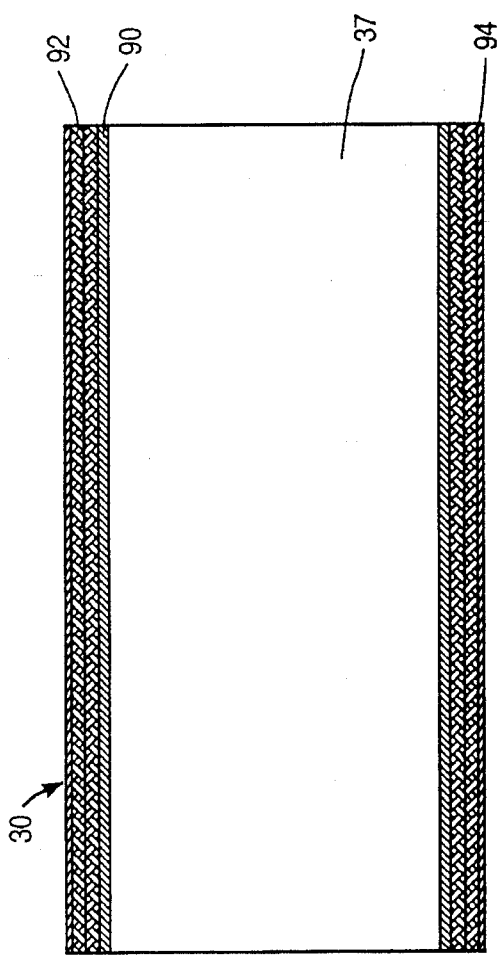

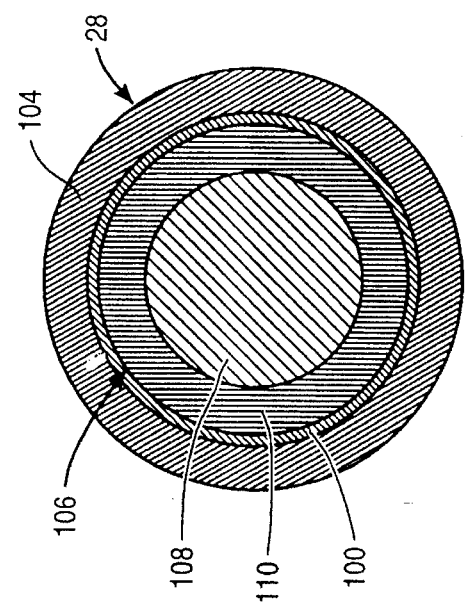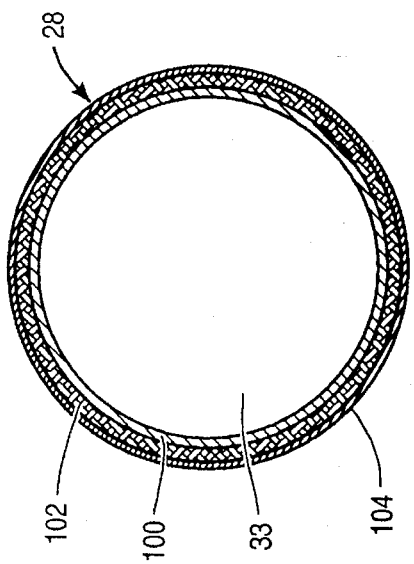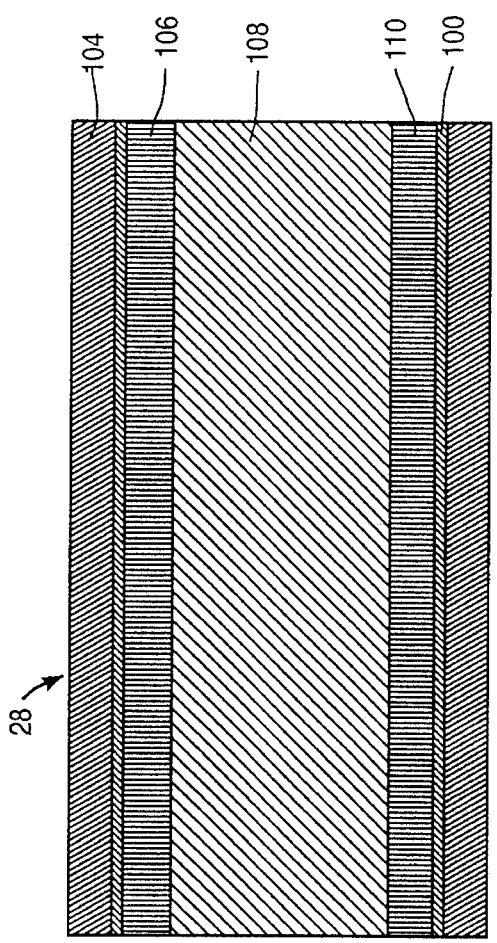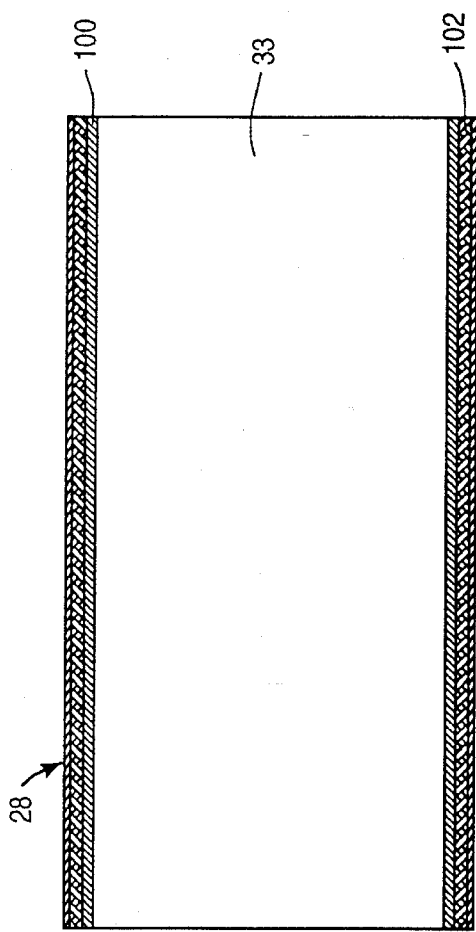

ATHERECTOMY CATHETER AND METHOD

This is a continuation of application Ser. No. 08/089,957, filed Jul. 9, 1993, now abandoned.

BACKGROUND OF THE INVENTION

The present invention relates generally to catheters for introduction into a patient's vascular system and methods of constructing such catheters. In particular, the present invention relates to an atherectomy catheter having a plurality of concentrically arranged shafts, the shafts having a multi layer torsionally reinforced construction for improved torsional stiffness and positionability, low profile and improved manufacturability.

Arteriosclerosis is a well-known disease of the vascular system in which fatty deposits, or atheroma, are deposited on the intimal lining of the patient's blood vessels. This can result in stenotic regions which may partially or completely occlude the vessel, inhibiting blood flow through the vessel. Arteriosclerosis may produce a variety of health consequences, including angina, hypertension, myocardial infarction, and strokes.

Various devices have been developed for treatment of arteriosclerosis. One such device which has shown promising results is the atherectomy catheter. Such catheters typically comprise an elongated, flexible body having a device on its distal end designed to sever stenotic material from the vessel wall. A balloon is frequently mounted at the distal end to assist in positioning directional severing device against the vessel wall. The catheter is inserted into an artery and advanced through the artery to the desired treatment site with the balloon in a deflated configuration. Rotational positioning is usually required in order to properly position the severing device adjacent the stenotic material to be excised. Such rotation is usually accomplished by exerting torque on the proximal end of the catheter so as to twist the distal end to the desired position. An inflation fluid is then supplied to the balloon through a lumen in the catheter body so as to expand the balloon and position the severing device against the vessel wall.

The severing devices which have been used in such atherectomy catheters have taken various forms. Of particular interest to the present invention is the use of a cylindrical or helical cutting blade which is rotatably mounted in a housing at the distal end of a catheter body. A drive shaft extends from the proximal end of the catheter body through a lumen to the distal end where it is coupled to the cutting blade. A drive motor at the proximal end rotates the drive shaft so as to turn the blade. Usually, the blade will be partially exposed through an opening on one side of the housing. Tissue may be positioned in the opening and the blade advanced against the tissue as it is rotated so as to sever the tissue. The opening is rotationally positioned within the vessel by exerting torque on the proximal end of the catheter body, so as to turn the housing until the opening is properly positioned adjacent the stenotic material to be severed. A balloon is typically mounted on the housing opposite the opening, such that the opening can be positioned against the vessel wall when the balloon is expanded.

Atherectomy catheters must be constructed in such a way that they have an appropriate degree of flexibility as well as a low profile (i.e. small diameter) so as to be positionable in a blood vessel. At the same time, such catheters must have suitable torsional stiffness to facilitate rotational positioning of the opening in the housing which exposes cutting device by exerting torque on the proximal end. Such catheters will usually have multiple lumens, including a lumen for introducing an inflation fluid to the balloon, a guide wire lumen which receiving a movable guide wire as the catheter is advanced to navigate the vessel, as well as a lumen through which the drive shaft of the cutting blade may be rotationally disposed. The achievement of a catheter with the desired flexibility, torsional rigidity, small profile and durability in a way which is durable and manufacturable at low cost is a challenge.

In particular, the configuration of the lumens in known catheters has resulted in a somewhat complex structure which is costly to manufacture. For example, the inflation lumen, drive shaft lumen and guide wire lumen in known devices are often formed as separate lumens and arranged in parallel along the length of the catheter body.

In addition, known manufacturing techniques for producing catheters having enhanced torsional rigidity have suffered from certain drawbacks. One known method for producing a catheter body with enhanced torsional rigidity involves imbedding a pattern of a reinforcing material, such as braided wire or fibers, into the wall of a tubular polymer shaft. Typically, the reinforcing material is positioned over a mandril having an inside diameter of the desired finished dimension. A second layer of polymeric material is extruded over the reinforcing material so that the reinforcement is encapsulated within the resulting polymeric wall of the catheter body.

An improvement on this method for imbedding reinforcement material in the wall of the catheter body is described in U.S. Pat. No. 4,764,324 to Burnham (the '324 patent), the complete disclosure of which is incorporated herein by reference. The improved method involves placing the reinforcing material, such as a wire braid or helical wrap, over a polymer tube and heating the tube while simultaneously applying axial tension to the reinforcement. This causes the reinforcement to penetrate beneath the surface of the polymer tube, and the penetration depth is controlled by controlling the temperature of the catheter body and the tension exerted on the reinforcing material. Once the reinforcing material is submerged to the proper depth in the tube, the waffled outer contour of the tube caused by the impregnation of the reinforcing material is smoothed to the desired dimension by passing the substrate through a die.

While the extrusion technique described in the '324 patent may have certain advantages, the method suffers from difficulty in controlling the dimensions of the catheter wall and the depth to which the reinforcing material penetrates.

Where a rotatable cutting blade is utilized in an atherectomy catheter as described above, the lumen through which the drive shaft or cable is disposed should have a suitable degree of lubricity to permit the shaft to rotate with minimal friction even when the catheter is configured in a tortuous path in the vessel. One known technique for providing a low friction surface on the catheter lumen wall is described in U.S. Pat. No. 4,898,591, the complete disclosure of which is incorporated herein by reference. A lubricious hydrogel coating of a biocompatible material such as a copolymer of polyurethane and polyvinyl pyrrolidone is applied to the surface of the catheter lumen by flushing the hydrogel solution through the lumen of the catheter, dipping the catheter in a bath of the solution or spraying the solution onto the desired surfaces, followed by drying and curing in an oven. This technique is labor-intensive and increases manufacturing costs.

An improved atherectomy catheter is therefore desired which is highly flexible for positioning in the vascular system, while having high torsional rigidity for rotational positionability. The catheter should have a low profile, and preferably be round in cross section to facilitate positioning within the confines of a blood vessel. Particularly desirable is a catheter which is manufacturable using low-cost, automated processes, capable of repeatably and accurately controlling catheter dimensions and quality. In particular, the catheter should have a torsionally reinforced body, capable of including at least three lumens, one through which an inflation fluid may be introduced, one in which a rotatable drive shaft or cable may be disposed, and a third through which a movable guide wire may be inserted. The drive shaft lumen should have a low-friction surface in contact with the drive shaft to facilitate low-friction rotation of the drive shaft with the catheter in various longitudinal configurations. In addition, the inflation lumen should be comprised so as to be very durable, resisting puncturing during manipulation.

DESCRIPTION OF THE BACKGROUND ART

Methods of catheter construction are described in U.S. Pat. Nos. 4,764,324 and 4,898,591. Atherectomy catheters employing a rotatable cutting blade for severing stenotic tissue are described in U.S. Pat. Nos. 4,669,469; Re. 33,569; 4,781,186; 4,926,858; 4,979,951; 5,047,040; 5,071,425; 5,084,010; and 5,092,873. A catheter introducer with a flexible tip is described in U.S. Pat. No. 4,950,257. The complete disclosures of the foregoing patents are incorporated herein by reference.

SUMMARY OF THE INVENTION

In a first aspect of the present invention, a catheter comprises a housing shaft having a proximal end, a distal end and a lumen therebetween. The shaft includes a torsionally reinforced polymeric outer layer over an unreinforced polymeric inner layer. An inflation tube is disposed over the housing shaft to define an annular inflation lumen between the inflation tube and the housing shaft. A housing is attached to the distal end of the housing shaft, and interventional means are disposed on a first side of the housing. Means for urging the housing toward the vessel wall, which may comprise an inflatable balloon, is attached to a second side of the housing and is in communication with the inflation lumen. Usually, the interventional means will comprise means for severing tissue, such as a cylindrical, helical, or other rotatable cutting blade. The interventional means will be rotatably positionable, and engagement of the means with stenotic tissue is achieved by activating the urging means attached to the opposing side of the housing. Catheters of the present invention thus have a simplified construction, and are manufacturable at relatively low cost. Moreover, through the use of a torsionally reinforced polymeric outer layer over an unreinforced polymeric inner layer, the housing shaft provides the torsional rigidity desirable for improved rotational positioning of the distal end of the catheter by exerting torque on the proximal end. Through similar construction, the inflation tube is made very durable.

In a preferred embodiment, the inner layer of the housing shaft will comprise a polymer having a first melting point, and the outer layer of the housing shaft will comprise a polymer having a second melting point, the second melting point being lower than the first melting point. The outer layer may thus be heated to its melting point, without melting the inner layer. At such a temperature, the outer layer may be impregnated with reinforcement material, such as a wire braid. In an exemplary embodiment, the inner layer is a relatively hard, lubricous polymer taken from the class of low coefficient of friction polymers such as a fluorocarbon polymers, e.g. polytetrafluoroethylene (PTFE) or fluorinated ethylenepolypropylene (FEP), available commercially from DuPont under the trademark Teflon, which have a suitably high melting point and provide a low-friction surface within which other movable components of the catheter, such as the drive shaft as described below, may be disposed.

In a further preferred embodiment, a drive shaft will be rotatably disposed in the lumen of the housing shaft. Usually, the drive shaft will be coupled to a cutting blade disposed in the housing at the distal end. At the proximal end, the drive shaft will be coupled to a drive motor. The drive shaft may be any of a variety of known constructions, but in a particular embodiment, will be constructed in a manner like that of the housing shaft, with a torsionally reinforced outer layer and an unreinforced inner layer. As with the housing shaft, the inner layer will preferably be a relatively hard, lubricous polymer and the outer layer will be a polymer-encapsulated wire braid. Such a construction is advantageous since the drive shaft should be able to deliver relatively high torsional loads (to the cutting blade or other device) while retaining bending flexibility, just as with the housing shaft.

Usually, the drive shaft will have a longitudinal guide wire lumen through which a movable guide wire may be inserted for guiding the catheter into a vessel. In such cases, the lubricous inner layer is a particular advantage since it facilitates passage of the guide wire.

In a still further preferred embodiment, the inflation tube will also be constructed to have a unreinforced polymeric inner layer and a torsionally reinforced polymeric outer layer concentrically fixed to the inner layer. As in the case of the housing shaft and/or the drive shaft, the inflation tube, in an exemplary embodiment, will have an unreinforced inner layer and an outer layer of a polymer-encapsulated wire braid. The lamination provides extremely good durability to resist leaks in the inflation tube. In addition, the low friction lining may enhance infusion of the inflation fluid.

In a second aspect of the present invention, a catheter comprises a housing shaft with a proximal end, a distal end and a lumen therebetween, and an inflation tube disposed concentrically over the housing shaft to define an annular inflation lumen therebetween, the inflation tube having a first bending stiffness. A housing is attached to the distal end of the housing shaft, the housing having a second bending stiffness. A transition tube is connected between the distal end of the inflation tube and the proximal end of the housing, the transition tube having a third bending stiffness. A transition lumen extends through the transition tube in communication with the inflation lumen. Interventional means is disposed on a first side of the housing, and means for urging the housing toward the vessel wall is attached to a second side of the housing in communication with the transition lumen. Preferably, the third bending stiffness (of the transition tube) is less than the first bending stiffness (of the inflation tube), and the first bending stiffness is less than the second bending stiffness (of the housing). This provides a transitional section of the catheter from the flexible inflation tube to the relatively stiff housing, for an improved connection therebetween. Usually, the housing shaft will comprise a torsionally reinforced outer layer laminated to an unreinforced inner layer, as described above. The inflation tube may also have this construction. The transition tube will usually comprise an unreinforced polymer. The housing may be any of a variety of materials, but in an exemplary embodiment, will be a metal such as stainless steel.

Usually, the housing shaft will extend through the transition tube and will attach to the proximal end of the housing. A portion of the interior of the transition tube will be fixed to the periphery of the housing shaft, leaving a partial annular space which defines the transition lumen connecting the inflation lumen to the urging means. In a preferred embodiment, the urging means will be an inflatable balloon.

As in the embodiment described above, a drive shaft may be disposed in the lumen of the housing shaft for driving a cutting blade disposed in the housing of the catheter. The drive shaft may be constructed of a torsionally reinforced outer layer formed over an unreinforced inner layer. The drive shaft may further include a guide wire lumen through which a movable guide wire may be inserted.

In another aspect of the present invention, a method for making a catheter includes the steps of providing a inner tubular layer of a first polymer having a first melting point; forming over the inner layer an outer layer of a second polymer having a second melting point, the second melting point being lower than the first melting point; heating the outer layer to a temperature of at least the second melting point and less than the first melting point; and embedding a reinforced structure, typically a wire braid, into the outer layer until it reaches the inner layer.

In one embodiment, the first melting point is between 500° F. and 800° F., and the second melting point is between 200° F. and 500° F. The inner layer will preferably comprise a fluorocarbon polymer, such as PTFE or FEP. The second, or outer, layer will comprise, in an exemplary embodiment, a polyether-amide block copolymer/polyamide blend which is impregnated with the wire braid. The wire braid may be, for example, stainless steel. In a further embodiment, the method may further comprise a step of extruding the inner layer before forming the outer layer. The inner layer may be extruded over a mandril which can be removed after processing, leaving a longitudinal lumen within the shaft.

The method may also include a step of reheating the outer layer to the second melting point and impregnating the outer layer with a second wire braid, which will overlie the first wire braid. Such a step is particularly useful in forming the housing shaft of the catheter of the present invention, which desirably has high torsional rigidity. This method not only reinforces the outer layer, but the simultaneous heat and pressure of the reinforcing material sinking through the outer layer to contact the inner layer aids in improving the lamination of the two layers.

The method may also include a step of roughening the outer surface of the inner layer before the outer layer is formed, so as to improve adhesion between the inner and outer layers. Usually, this roughening is performed by chemically etching the outer surface of the inner layer.

The device and method of the present invention provide a catheter which has increased torsional rigidity for improved rotational positioning, precisely controllable dimensions, low profile, and low-cost manufacturability. A further understanding of the nature and advantages of the invention may be realized by reference to the remaining portions of the specification and the drawings.

BRIEF DESCRIPTION OF THE DRAWINGS

FIGS. 3A and 3B are side cross-sectional and detail views of the transition tube of the catheter of FIG. 1.

FIGS. 9A–9D are side cross-sectional views of the housing shaft of the catheter of FIG. 1.

FIGS. 10A–10D are side cross-sectional view of the inflation tube of the catheter of FIG. 1.

DETAILED DESCRIPTION OF THE SPECIFIC EMBODIMENTS

A catheter constructed in accordance with the principles of the present invention is illustrated in FIG. 1–10. While the present invention will be described with specific reference to a catheter adapted for use as an atherectomy device, the principles of the invention will have equal applicability to a variety of catheter devices where torsional rigidity, flexibility, low cost and repeatable manufacturability are desirable.

Figure 1:
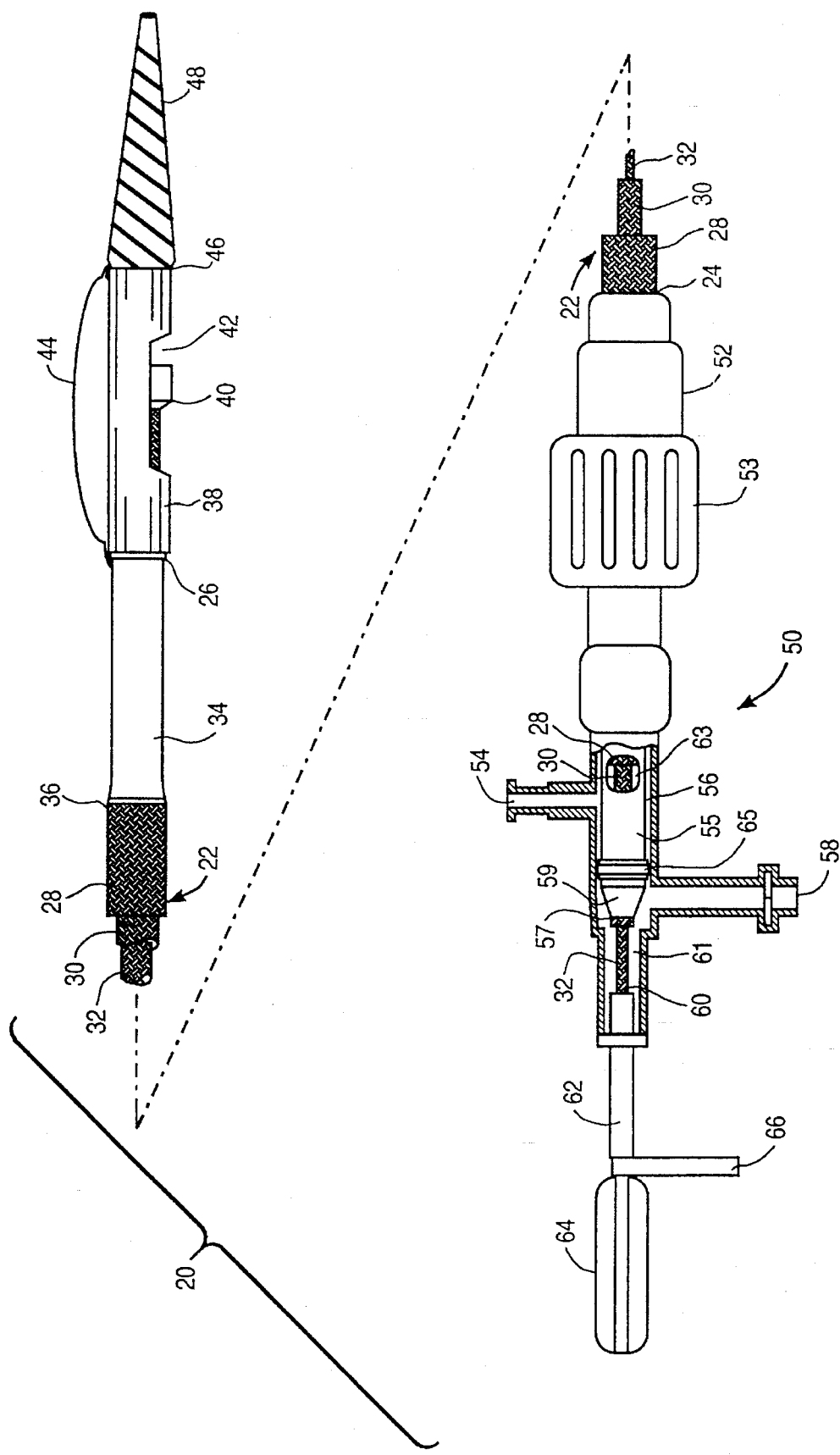
FIG. 1 is a side elevational view of a catheter constructed in accordance with the principles of the present invention with portions broken away.

Referring to FIG. 1, atherectomy catheter 20, in a preferred embodiment, includes an elongate catheter body 22 having a proximal end 24 and a distal end 26. Catheter body 22 includes an inflation tube 28, a housing shaft 30, and a drive shaft 32 arranged generally concentrically. A transition tube 34 is attached to the distal end 36 of inflation tube 28. The transition tube 34 encapsulates a transition lumen and the housing shaft 30 to which is attached a housing 38 at distal end 26. Interventional means 40 are disposed within housing 38 and exposed through an opening 42 on a first side of the housing 38. On a second side of the housing opposite opening 42, a means for laterally urging or deflecting the housing toward the vessel wall, typically a balloon 44 is attached. At the distal end 46 of the housing 38, a flexible nose-cone 48 is mounted.

Catheter body 22 is attached at its proximal end 24 to a proximal assembly 50. Proximal assembly 50 includes a distal strain relief 52, an inflation port 54 in communication with a first interior chamber 56, and a one-way flush valve 58 in communication with a second chamber 61. Drive shaft 32 connects at its proximal end 60 to a shaft extension 62 fixed to a spline 64. Spline 64 may be coupled to a drive motor for rotating drive shaft 32, as described more fully below. An advancement control lever 66 extends laterally from shaft extension 62 and is rotationally decoupled therefrom so as to be independent of the rotation of spline 64, extension 62 and drive shaft 32. Advancement control lever 66 facilitates the application of an axial force to drive shaft 32 so as to move interventional means 40 in an axial direction, as will be described below.

Figure 2:
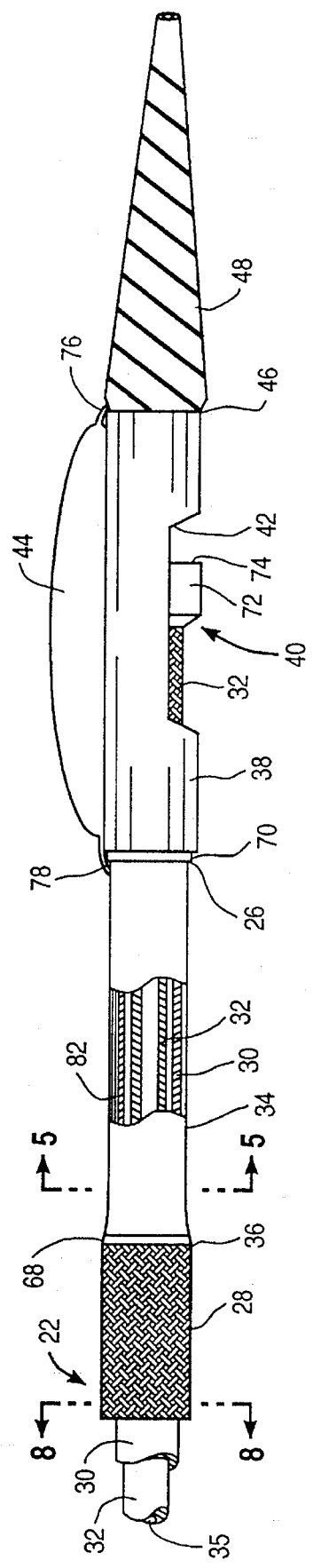
FIG. 2 is a side elevational view of a distal portion of the catheter of FIG. 1 with portions broken away.
Figure 4:
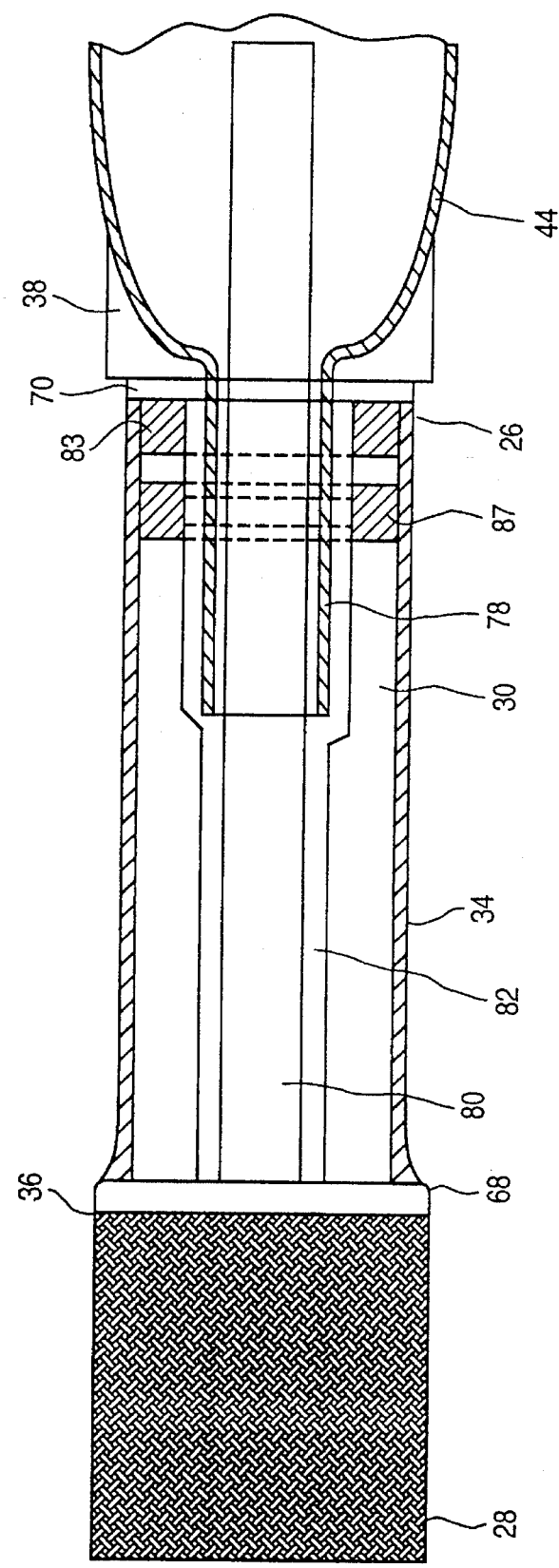
FIG. 4 is a top cutaway view of the transition tube of the catheter of FIG. 1.

Referring now to FIG. 2, the inflation tube 28 is attached at its distal end 36 to the transition tube 34, and terminates with an end ring 68. The housing shaft 30 extends through transition tube 34 and is attached to the housing 38 by means of tailpiece 70. Transition tube 34 is at least partially laminated to the periphery of housing shaft 30. The drive shaft 32 is rotatably disposed concentrically within the housing shaft 30 and extends through the transition tube 34 into the housing 38 where it is coupled to the interventional means 40. In a preferred embodiment, the interventional means 40 comprises a cylindrical cutting blade 72 fixed to the distal end of the drive shaft 32. Distal end 74 of the cutting blade will have a sharpened edge which, by rotation of blade 72, facilitates severing stenotic tissue. Blade 72 and drive shaft 32 are further slidably disposed within housing 38 so as to be movable in an axial direction within opening 42.

Nosecone 48 fixed to distal end 46 of housing 38 will be composed of a flexible material, such as a stainless steel spring encapsulated in a polymer. Suitable nosecone constructions and ways for attachment to the housing 38 are described in detail in co-pending application Ser. No. 07/823,905, the full disclosure of which is incorporated herein by reference.

Housing 38 may be either flexible or rigid, but will usually be more rigid than the catheter body 22. The construction of flexible housings is described in U.S. Pat. No. 4,781,186, the complete disclosure of which is incorporated herein by reference. In a particular embodiment, however, the housing will be a rigid material such as stainless steel or rigid plastic, as described in U.S. Pat. No. 5,071,425, the complete disclosure of which is incorporated herein by reference. The length of the housing is not critical, typically in the range from about 10 mm to 50 mm, usually being in the range from about 12 mm to 40 mm. The opening 42 will typically have a length in the range from about 5 mm to 45 mm and a width in the range from about 1 mm to 4 mm.

Cutting blade 72 may be cup shaped as illustrated, or may have a variety of other configurations. Particular alternate configuration include helical blades, as shown in U.S. patent application Ser. No. 07/971,697, the disclosure of which is incorporated herein by reference and barrel cutters, as shown in U.S. patent application Ser. No. 07/604,036, the disclosure of which is incorporated herein by reference. Motorized means for rotating and translating the blade 72 are described in U.S. Pat. No. 4,771,774, and co-pending application Ser. No. 07/982,814, both of which are incorporated herein by reference.

Means 44 for urging the housing against a vessel wall is mounted on housing 38 on a side opposite opening 42. In a preferred embodiment means for urging 44 is an inflatable balloon. The construction of such balloons is described in U.S. Pat. No. Re. 33,561, and U.S. Pat. No. 5,092,873, the complete disclosures of which are incorporated herein by reference. The balloon 44 will usually be composed of polyethylene terephthalate (PET). Balloon 44 has a distal tab 76 which is inserted into the joint between the housing 38 and nose-cone 48 to secure the distal end of the balloon. Usually, the balloon 44 will be transparent and formed integrally as an expanded portion of a lumen of a flexible tube, referred to herein as a balloon leg 78, which extends proximally from the balloon into the transition tube 34, as described more fully below. Typically, the balloon 44 will have a width, when fully inflated, of approximately 1 mm to 6 mm, more typically in the range of about 2 mm to 4 mm. The balloon will usually be attached to housing 38 by an adhesive. Balloon 44 may or may not be vented, the preferred embodiment of FIG. 2 shown unvented.

Referring to FIGS. 3–6, the construction of the transition tube 34 will be described in greater detail. Transition tube 34 will usually be a polymer, such a polyetheramide block copolymer thermoplastic elastomer with high thermal stability at temperatures within a range around that of the human body. Such polymers are commercially available from suppliers such as Atochem of Philadelphia, Pa., under the tradename PEBAX. The transition tube will preferably have a stiffness or hardness which is lower than that of the catheter body 22 and housing 38. In an exemplary embodiment, the transition tube has a shore D hardness of about 40 to 60. The transition tube is laminated to the inflation tube 28 and housing shaft 30, usually by melting the transition tube 34 into the inflation tube 28 and housing shaft 30. An end ring 68 of polyethylene terephthalate (PET) shrink tubing terminates inflation tube 28, as described more fully below.

Figure 5:
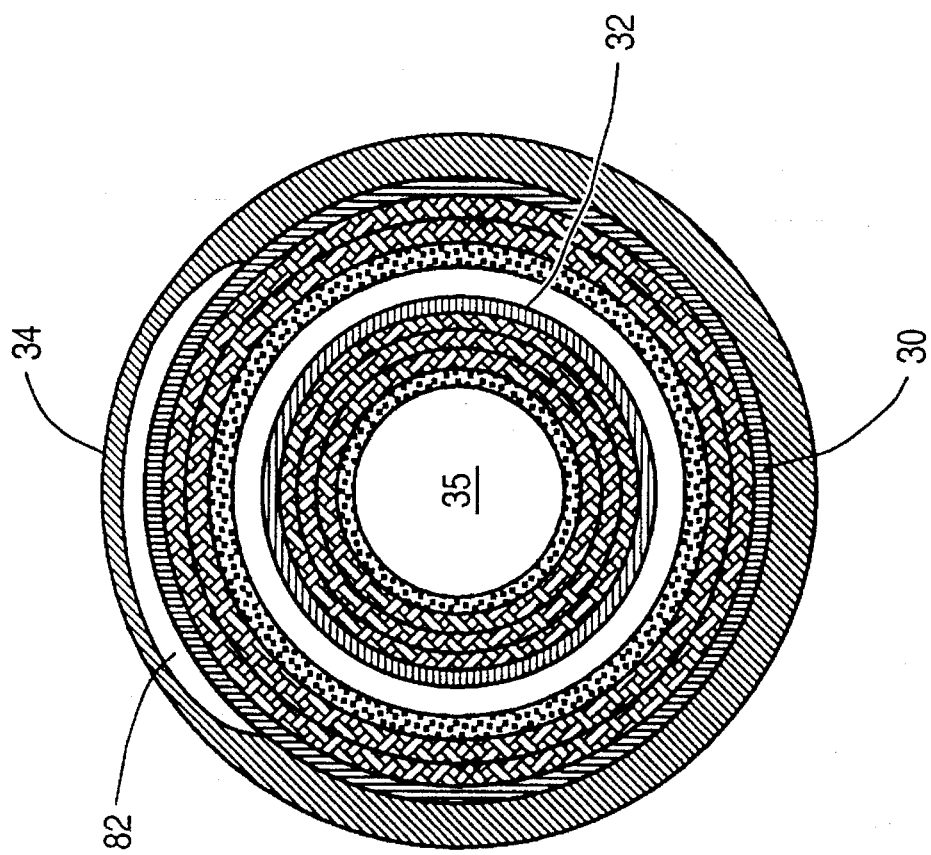
FIG. 5 is a transverse cross-sectional view through the transition tube of the catheter of FIG. 1.

Housing shaft 30 extends through the interior of transition tube 34, connecting at its distal end 26 to housing 38 by means of tailpiece 70 (see FIG. 6, described below). The interior surface of transition tube 34 is laminated to the exterior surface of housing shaft 30 about a portion of the periphery of the housing shaft 30. A portion, however, remains unlaminated and spaced apart from the housing shaft 30 to define a partially-annular transition lumen 82 between a portion of transition tube 34 and housing shaft 30, as best seen in FIG. 5. As illustrated in FIGS. 3A and 3B, this lamination will usually be accomplished by melting the transition tube 34 into the housing shaft 30, while a mandril 80 is maintained between the transition tube 34 and the housing shaft 30 in the region where transition lumen 82 will be formed. Typically, mandril 80 will be a fluorocarbon polymer, with an extremely low frictional coefficient and a high melting point. Mandril 80 extends from the interior of balloon 44 through balloon leg 78 and through transition lumen 82 into catheter body 22 between inflation tube 28 and housing shaft 30. In the distal region of transition tube 34 there is a PEBAX sealing ring 83 just proximal to the housing to improve sealing of the balloon leg 78. Also, two anchor rings of PET shrink tubing are added to prevent movement and to provide strain relief. The inner anchor ring 85 goes under the balloon leg 78, and the outer anchor ring 87 goes over the balloon leg, to hold it firmly in place and prevent leakage. Once lamination of transition tube 34 is complete, mandril 80 may be removed, leaving the transition lumen 82 and balloon leg 78 open, as illustrated in FIG. 5.

Transition tube 34 provides several important benefits lacking in previous catheter designs. In particular, the transition tube 34 provides a transition lumen 82 (shown in FIG. 7) which is available for actuating a lateral deflection mechanism on the housing 38. Typically, the transition lumen 82 will be an inflation lumen and the deflection mechanism will be an inflatable balloon, but the transition tube 34 could be advantageously employed with other designs, such as mechanical deflection mechanisms. The transition lumen 82 thus provides a sealed connection to the balloon leg 78, which is offset on one side of the device (as shown in FIG. 3A). In known catheters, the inflation lumen (which is generally non-annular) is typically connected to the balloon and attached to the exterior of the catheter body. This attachment method gives the distal portion of the catheter body a non-circular profile which detracts from positionability. In addition, the exterior attachment of such tubes makes them vulnerable to puncture or other damage. Further, the attachment of inflation lumen and balloon is usually by means of epoxy or other adhesives, which cannot be applied with sufficient precision during manufacturing to produce repeatable dimensions. The transition tube 34 of the present invention, by contrast, provides a strong and durable connection between the balloon 44 and inflation lumen 33 without the use of adhesives. The transition tube 34 connects the annular inflation lumen 33 to the non-annular, offset balloon leg 78 while maintaining the circular profile of the catheter body 22 continuously to the housing 38. The laminated polymeric construction and coaxial arrangement of the transition tube 34 further provide a well-protected transition lumen 82, unsusceptible to puncture or other damage. Of further benefit is the ability to vary the rigidity or bending stiffness of the transition tube 34 by changing its material or thickness, so as to tailor the flexibility of the distal end of the catheter body as appropriate for the particular procedure or anatomical structure in which the catheter will be used.

Figure 6:
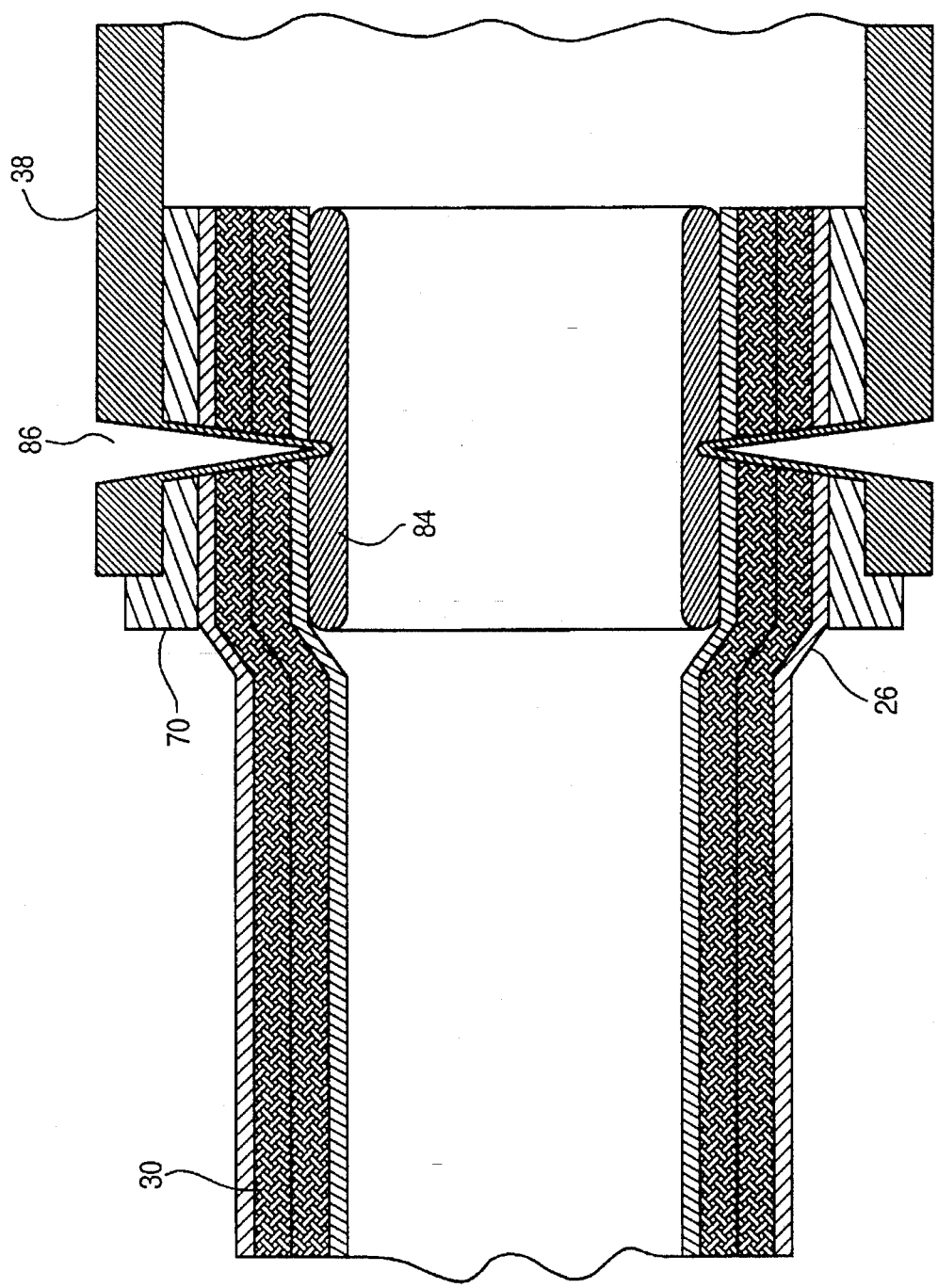
FIG. 6 is a cross-sectional view of a distal portion of the housing shaft and a proximal portion of the housing of FIG. 1.

Referring now to FIG. 6, the connection between the housing 38 and the housing shaft 30 will be described. It should be noted that transition tube 34, drive shaft 32, and balloon 44 are not shown in FIG. 6 for purposes of clarity. In a preferred embodiment, the housing 38 is attached to the housing shaft 30 by a press fit attachment method, utilizing an inner ring 84, the tailpiece 70 and the housing 38. Using this method, the distal end 26 of the housing shaft 30 is flared slightly outward, so that the inner ring 84 may be pressed into the interior diameter of the housing shaft 30 as the tailpiece 70 is simultaneously pressed over the outer diameter of the housing shaft 30. Housing 38 is then slipped over the tailpiece 70, and dimples 86 are formed which deform the housing 38, the tailpiece 70, and the housing shaft 30 radially inward to engage inner ring 84. This creates a strong and durable connection.

Figure 7:
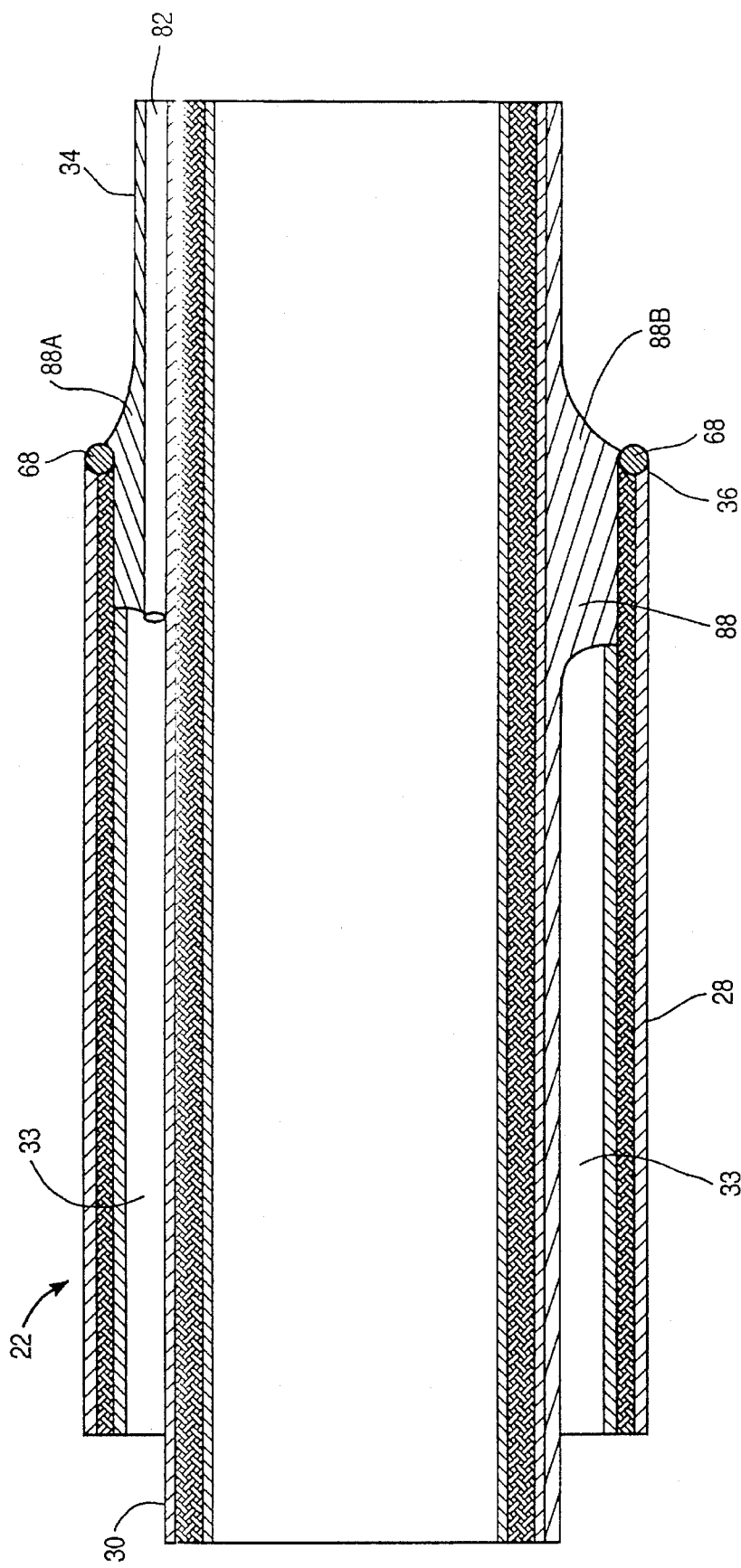
FIG. 7 is a side cross-sectional view of a distal portion of the inflation tube and housing shaft at the point where it connects to the transition tube of the catheter of FIG. 1.

FIG. 7 illustrates the connection of the transition tube 34 to the distal end 36 of the inflation tube 28. For purposes of clarity, drive shaft 32 is not shown in FIG. 7. As will be more fully described below, the housing shaft 30 is disposed within inflation tube 28 so as to define an annular inflation lumen 33 between the housing shaft 30 and inflation tube 28. Transition lumen 82 of transition tube 34 must be in communication with inflation lumen 33 so that inflation fluid may be introduced through the inflation lumen 33 and the transition lumen 82 to the balloon 44. As described above, during the process of laminating the transition tube 34 to the inflation tube 28 and the housing shaft 30, the mandrill 80 will be inserted through inflation lumen 33 so as to extend into transition lumen 82 thereby maintaining the patency of both lumens. The transition tube/inflation tube connection is accomplished by inserting the proximal end 88 of the transition tube over the outer diameter of inflation tube 28. Heat is then applied, using a radio frequency magnetic induction heating system in one embodiment, so as to melt the PEBAX layer of the transition tube 34 into the inflation tube 28 as well as the outer surface of the housing shaft 30, forming a monolithic joint between the inflation tube, housing shaft and transition tube in regions 88a, 88b. It should be noted that, in region 88a, the patency of transition lumen 82 is maintained so as to be in communication with inflation lumen 33, whereas in region 88b, the annular inflation lumen is sealed by the PEBAX joint. During the lamination process, end ring 68 on inflation tube 28 ensures that the reinforcing braid within the inflation tube 28 (described below) is retained in an encapsulated position within the wall of inflation tube 28.

Figure 8:
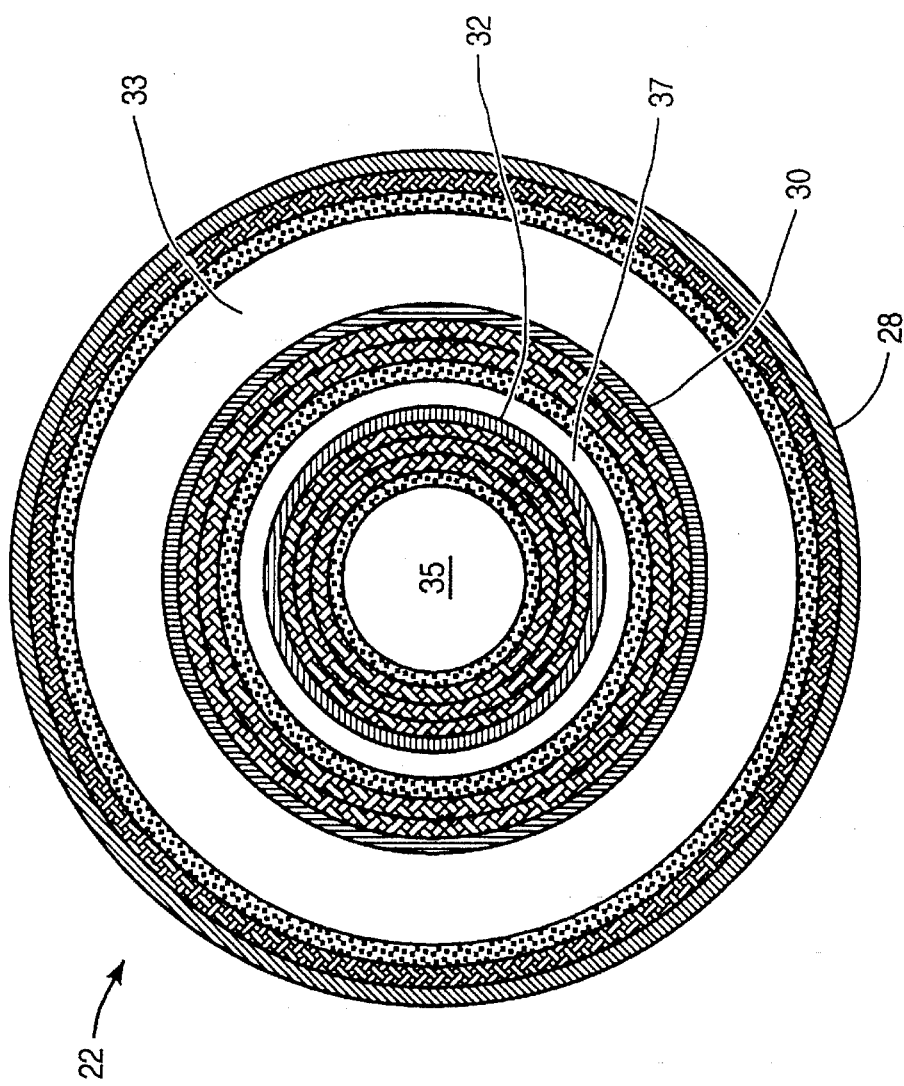
FIG. 8 is a transverse cross-section through the body of the catheter of FIG. 1.

The construction of the body 22 of the catheter of the present invention will now be described with reference to FIGS. 8–10. FIG. 8 illustrates a transverse cross section of catheter body 22. Body 22 may be described as triaxial, with housing shaft 30 disposed concentrically within inflation tube 28 to define annular inflation lumen 33, and drive shaft 32 disposed within lumen 37 of housing shaft 30. Drive shaft 32 has a longitudinal guide wire lumen 35 through which a movable guide wire of conventional construction may be inserted. Drive shaft 32 will be rotatably disposed within housing shaft 30 to facilitate rotation of cutting blade 72, best seen in FIG. 2.

Catheter body 22 is of a size suitable for positioning within a vessel, typically an artery. In an exemplary embodiment, the inflation tube will have an inner diameter (ID) of about 0.07 inches and an outer diameter (OD) of about 0.08 inches, the housing shaft will have an ID of about 0.043 inches and an OD of about 0.06 inches, and the drive shaft will have an ID of about 0.018 inches and an OD of about 0.035 inches. Of course, these dimensions will vary according to the particular procedures for which the catheter is designed.

Referring now to FIGS. 9A–9D, the construction of the housing shaft 30 will be described. Housing shaft 30 comprises an inner layer 90 of a polymeric material, usually a fluorocarbon polymer such as PTFE or other low coefficient of friction material, over which is braided two layers of reinforcement wire 92, usually stainless steel, shown in FIGS. 9C–9D. The reinforcement is completely encapsulated within a polymeric outer layer 94, which in an exemplary embodiment will comprise a thermoplastic elastomer such as PEBAX 5533 and Nylon 12 a medical grade polyether-amide block copolymer blend with a Shore D durometer of about 60. Depending upon the degree of torsional rigidity desired, one, two or more layers of braided reinforcement may be used.

The present invention further provides a method of making a catheter shaft, which can be used as the housing shaft 30, inflation tube 28 and, if desired, drive shaft 32. According to the method of the invention, a base construction of a mandril 96 is provided, over which a layer of polymeric material is extruded. This extruded layer forms inner layer 90 of housing shaft 30. Material selected for inner layer 90 may be any of a variety of polymers, the essential characteristics being that the polymer have a sufficiently high melting point to remain solid when heat is applied to the polymeric outer layer, as described below. The inner layer should further have a relatively low coefficient of friction, preferably in the range of 0–0.4, to facilitate free rotation of the drive shaft 32 within lumen 37 or to increase the durability of the inflation tube 28. The preferred material is PTFE, as described above but may comprise a variety of low friction materials including other fluorocarbon polymers.

An outer layer 94 of a polymer, usually a PEBAX/Nylon blend or other polyamide and/or polymer blends, is preferably extruded over the inner layer 90, but in some cases it may be acceptable to place a preformed tube over the inner layer followed by the heat lamination. The material selected for the outer layer 94 will usually be a thermoplastic polymer having a melting point which is lower than that of inner layer 90, so as to facilitate embedding of outer layer 94 with reinforcement wire (by melting the outer layer without melting the inner layer). In a preferred embodiment, the inner layer 90 will have a melting point within the range of 500° F. to 800° F. while the outer layer 94 will have a melting point within the range of 200° F. to 500° F.

In one specific embodiment, the mandril 96 will have a diameter of approximately 0.043 inches, inner layer 90 will have a thickness of about 0.002 inches, and outer layer 94 will have a thickness of about 0.012 inches. These dimensions, of course, will vary with particular applications. This base construction comprising mandril, inner layer and outer layer can be spooled in a continuous length for further processing.

The base construction is then passed through a first layer of braided reinforcement, which usually will be stainless steel wire. Forced hot air melts the outer layer 94 as it passes into the braid cone, allowing the braid wire to sink into the melted outer layer 94 down to the inner layer 90, which remains intact due to its higher melting point. Once the first layer of braid has been impregnated into outer layer 94, the construction is passed through a second braid layer, and the outer layer 94 reheated to impregnate the second braid layer into the outer layer down to the first braid layer. Commercial equipment suitable for performing such continuous braiding operations is available from suppliers such as Steeger, U.S.A. of Spartanburg, S.C. A heated die is then used to appropriately size the outer diameter of the construction and provide a suitable surface finish.

The method may also include a step of roughening the outer surface of the inner layer 90 before the outer polymeric layer 94 is formed, so as to improve adhesion between the inner and outer layers 90. Usually, this roughening is performed by chemically etching the outer surface of the inner layer 90.

The completed construction, which may remain in a continuous length and spooled for convenience or which may be in discrete lengths, may be then loaded onto an automated cutting machine, which cuts the product to the desired length. Mandril 96 is then removed from housing shaft 30 leaving longitudinal lumen 37 in which the drive shaft 32 may be disposed.

The method of the invention thereby provides an automatable process for producing continuous lengths of braid-reinforced tubing with very low scrap rates, minimal machine set-up, ultra-thin walls, and precise dimensional control. In addition, simultaneous application of heat and pressure provide excellent adhesion between inner 90 and outer 94 polymeric layers. Particularly advantageous is the ability to precisely control the depth to which the reinforcement braid is impregnated into the wall of the shaft, through the use of an inner layer with a higher melting point, against which the braid may be positioned.

FIGS. 10A–10D illustrate the construction of inflation tube 28. Inflation tube 28 comprises a polymeric inner layer 100, usually of PTFE or other fluorocarbon polymer, surrounded by a braided reinforcement 102, shown in FIGS. 10C–10D, usually of stainless steel, which is encapsulated within a polymeric outer layer 104, preferably of PEBAX 5533. As with housing shaft 30, one or multiple layers of braided reinforcement may be provided, depending upon the degree of torsional rigidity desired in the inflation tube 28. Usually, the inflation tube 28 will be constructed to have less torsional rigidity than housing shaft 30 so that exerting torque at the proximal end of the catheter will be translated to the distal end primarily by the housing shaft 30. However, the inflation tube 28 will be provided with sufficient torsional rigidity so as to follow the rotation of the housing shaft 30, rather than twisting relative to it. The braided reinforcement 102 also adds hoop strength to resist crushing, as well as improves burst strength and durability.

The materials selected for the inflation tube 28 will be guided by considerations similar to those described above with reference to the housing shaft 30. Ordinarily, the materials selected will be similar to those for the housing shaft 30 to simplify processing. Thus, in an exemplary embodiment, inner layer 100 will be a fluorocarbon polymer such as PTFE Teflon, braided reinforcement 102 will be stainless steel, and outer layer 104 will be PEBAX 5533.

Inflation tube 28 will be manufactured according to the method described above used for the housing shaft 30. In some cases, it may be necessary to employ a blocker wire 106 of two-piece construction, due to dimensional restrictions of the processing equipment. Thus, in the embodiment shown in FIGS. 10A and 10B, mandril 106 includes a stainless steel wire 108 with an overcoating 110 of PTFE or FEP to facilitate handling in automated processing equipment.

When the inflation tube 28 has been constructed according to the method described above, cut to length and blocker wire 106 removed, several finishing steps may be performed.

A finishing step involves the application of an end ring 68 to the distal termination 36 of inflation tube 28 to retain the braid layer 102 during lamination of transition tube 34. The end ring 68, shown in FIG. 7, consists of a piece of PET heat shrink tubing. The end ring 68 is applied to the inflation tube 28 by inserting a mandril into the interior lumen 33 of the inflation tube 28, positioning the end ring 68 to overlap the end of the inflation tube 28 and exposing the end ring 68 to forced hot air. This shrinks the end ring 68 onto the inflation tube 28 and mandril. The end ring 68 and inflation tube 28 may then be trimmed to the desired length.

In an alternative embodiment, an additional finishing step for the inflation tube 28 is to apply a PET shrink tube (not shown) to a proximal portion of the inflation tube 28 to improve the column strength of this proximal portion for improved positionability and to assist in maintaining the patency of the inflation lumen 33 during manipulation of the catheter.

In a final step, a lubricous coating of Ultrax® or other low friction coating may be applied to a distal portion of the device, including housing 38, transition tube 34, and/or a distal part of the inflation tube 28.

Drive shaft 32 may be of conventional construction, like that described in U.S. Pat. No. 5,071,425, the disclosure of which has been incorporated herein by reference. Alternatively, the drive shaft 32 may be constructed using the method of the invention described above, with an inner polymeric layer, and an outer reinforced polymeric layer impregnated with a braided reinforcement. Depending upon the degree of torsional rigidity desired in the drive shaft 32, which normally will be relatively high, multiple layers of reinforcement braid may be used in the drive shaft 32. By utilizing the method of the present invention to form drive shaft 32, the guide wire lumen 35 extending longitudinally through the drive shaft will be lined with an inner polymeric layer typically of a fluorocarbon polymer, providing a low-friction surface through which a movable guidewire may be inserted for improved positioning of the device.

Referring again to FIG. 1, proximal assembly 50 includes a distal strain relief 52 at the point where catheter body 22 joins proximal assembly 50. A rotator 53 is rotationally coupled to proximal assembly 50, and a rotator tube 55 is secured to rotator 53 and extends in a proximal direction into a first interior chamber 56 in the assembly. Inflation tube 28 extends proximally through rotator 53 and is secured in a distal portion of rotator tube 55. Housing shaft 30 extends proximally through rotator tube 55 to a proximal end 57 thereof, where the housing shaft 30 is secured to rotator tube 55 by means of an epoxy fillet 59. In this way rotation of catheter body 22 (including housing shaft 30 and inflation tube 28) is accomplished by rotation of rotator 53 relative to proximal assembly 50.

Drive shaft 32 extends proximally through a second chamber 61 in the assembly, and is secured at its proximal end 60 to a shaft extension 62. Shaft extension 62 is attached to a spline adapter 64 configured to be coupled with a drive motor of the type described in U.S. patent application Ser. No. 07/982,814, the complete disclosure of which has been incorporated herein by reference. An advancement control lever 66 extends in the radial direction from shaft extension 62 and is rotationally decoupled therefrom. Advancement control lever 66 facilitates the application of axial force either distally or proximally on drive shaft 32 so as to axially translate interventional means 40 within housing 38.

An inflation fluid entry port 63 is disposed on a side of rotator tube 55 to provide fluid communication between first chamber 56 and annular inflation lumen 33 in inflation tube 28 (see, e.g., FIG. 8). An O-ring 65 disposed about a proximal end of rotator tube 55 seals first chamber 56 from second chamber 61. In this way, an inflation fluid introduced through inflation port 54 will be communicated into first chamber 56, through inflation fluid entry port 63 and into inflation lumen 33.

Second chamber 61 in proximal assembly 50 is in communication with lumen 37 (see FIG. 8) in housing shaft 30. A one-way flush valve 58 is in communication with second chamber 61. In this way, a flushing fluid may be introduced through flush valve 58 into second chamber 61, from which the flushing fluid will flow into lumen 37 in housing shaft 30.

It can be seen from the foregoing that the present invention provides a catheter of simplified construction, improved manufacturability and improved performance over known catheters. The method of the invention facilitates the construction of catheters having round cross section with greater torsional rigidity, very thin walls, and accurate control of dimensions. The catheter thus produced has a triaxial body which has the flexibility, torsional rigidity desirable in such devices. While the catheter is particularly adaptable for use as an atherectomy device, the catheter will be equally useful in any of a variety of instruments wherein an elongated, flexible body with enhanced torsional rigidity is desirable.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A catheter comprising:
   an inflation tube having a proximal end, a distal end, and an annular lumen therebetween;
   a housing shaft disposed in the annular lumen having a proximal end, a distal end, and a lumen therebetween;
   a drive shaft disposed in the lumen of the housing shaft having a proximal end and a distal end;
   a housing attached to the distal end of the housing shaft, the housing having an aperture on a first side thereof;
   a transition tube having a proximal end attached to the distal end of the inflation tube and a distal end attached to the distal end of the housing shaft, wherein a distal portion of the housing shaft extends through the transition tube to define a transition lumen therebetween in communication with the annular lumen at the proximal end of the transition tube;
   interventional means disposed in the housing and coupled to the distal end of the drive shaft, the interventional means operative through the aperture in the housing;
   means attached to a second side of the housing for urging the housing toward a vessel wall, the urging means being in communication with the transition lumen at the distal end of the transition tube; and
   wherein the transition lumen is disposed along a side of the transition tube generally aligned with said second side of the housing, and wherein the transition tube has a circular profile.

2. The catheter of claim 1 wherein the inflation tube comprises a torsionally reinforced polymeric outer layer.

3. The catheter of claim 2 wherein the inflation tube further comprises an unreinforced polymeric inner layer concentrically fixed to the outer layer.

4. The catheter of claim 3 wherein the inner layer comprises a first polymer having a first melting point, and the outer layer comprises a second polymer having a second melting point, the first melting point being higher than the second melting point.

5. The catheter of claim 4 wherein the first melting point is between 500° F. and 800° F. and the second melting point is between 200° F. and 500° F.

6. The catheter of claim 3 wherein the inner layer comprises tetrafluoroethylene or fluorinated ethylenepropylene.

7. The catheter of claim 2 wherein the outer layer of the inflation tube is impregnated with a wire braid.

8. The catheter of claim 1 wherein the transition tube is an unreinforced polymer.

9. The catheter of claim 1 wherein the housing is metal.

10. The catheter of claim 1 wherein the housing shaft comprises a torsionally reinforced polymeric outer layer over an unreinforced polymeric inner layer.

11. The catheter of claim 10 wherein the outer layer of the housing shaft is impregnated with a wire braid.

12. The catheter of claim 10 wherein the inner layer of the housing shaft has a coefficient of friction sufficiently low to allow free rotation of the drive shaft.

13. The catheter of claim 10 wherein the inner layer of the housing shaft comprises tetrafluoroethylene or fluorinated ethylene-propylene.

14. The catheter of claim 1 wherein the drive shaft comprises a torsionally reinforced outer layer and an unreinforced inner layer.

15. The catheter of claim 14 wherein the outer layer of the drive shaft is impregnated with a wire braid.

16. The catheter of claim 1 wherein the interventional means comprises a cutting blade rotatably disposed in the housing and coupled to the drive shaft.

17. The catheter of claim 1 wherein the means for urging comprises an inflatable balloon, the balloon having a tubular leg extending proximally from the balloon and encapsulated in the transition lumen.

18. A method of intravascular treatment comprising:
   positioning a housing at the distal end of a catheter near a treatment site in a vessel, the catheter including an inflation tube having an annular lumen, a housing shaft disposed in the annular lumen and having a drive shaft lumen, and a drive shaft disposed in the drive shaft lumen and having a guidewire lumen, the housing being attached to a distal end of the housing shaft, wherein the housing shaft comprises a reinforced polymeric outer layer over an unreinforced polymeric inner layer, the catheter further including a transition tube having a proximal end attached to the distal end of the inflation tube and a distal end attached to the distal end of the housing shaft, wherein a distal portion of the housing shaft extends through the transition tube to define a transition lumen therebetween in communication with the annular lumen at the proximal end of the transition tube, wherein the transition lumen is disposed along a side of the transition tube generally aligned with a balloon mounted to the housing, and wherein the transition tube has a circular profile;

delivering an inflation fluid through the annular lumen to the balloon so as to urge the housing toward a wall of the vessel such that stenotic material passes through an aperture in the housing; and axially translating the drive shaft to move a cutter axially across the aperture so as to sever stenotic material passing through the aperture.

19. The method of claim 18 further comprising rotationally positioning the housing by exerting torque on proximal end of the housing shaft so as to position the aperture in the housing adjacent the stenotic material.

20. The method of claim 18 wherein the inflation tube comprises a reinforced polymeric outer layer over an unreinforced polymeric inner.

21. The method of claim 18 further comprising rotating the cutter by rotating the proximal end of the drive shaft with a drive motor.

22. The method of claim 1 wherein the drive shaft comprises a reinforced polymeric outer layer over an unreinforced polymeric inner layer.

* * * * *